United States Patent [19]

Eidman et al.

[11] Patent Number: 4,797,503

[45] Date of Patent: Jan. 10, 1989

[54] CHIRAL 1-CYANOALKOXY 4-HYDROXYPHENYL DERIVATIVES

[75] Inventors: Kirk F. Eidman; David M. Walba, both of Boulder, Colo.

[73] Assignee: University Patents, Inc., Westport, Conn.

[21] Appl. No.: 144,001

[22] Filed: Jan. 15, 1988

Related U.S. Application Data

[63] Continuation of Ser. No. 880,851, Jul. 1, 1986.

[51] Int. Cl.$^4$ .......................................... C07C 121/52
[52] U.S. Cl. .................................................... 558/389
[58] Field of Search .......................................... 558/389

[56] References Cited

U.S. PATENT DOCUMENTS 4,505,929  3/1985  Markley et al. .................... 558/389

Primary Examiner—Mary C. Lee
Assistant Examiner—J. Richter
Attorney, Agent, or Firm—George M. Yahwak

[57] ABSTRACT

The preparation and properties of liquid crystal compounds having an achiral core and chiral tail units composed of the 1-cyanoalkoyl grouping (chiral cyanohydrin ethers) are described. The newly made compounds are shown to be useful as components of ferroelectric liquid crystal mixtures which exhibit high speed, multistate electro-optic switching properties making them ideally suited to certain electro-optic display device applications.

9 Claims, No Drawings

CHIRAL 1-CYANOALKOXY 4-HYDROXYPHENYL DERIVATIVES

This invention was made with partial Government support under Grant No. DMR-82-19529 awarded by the National Science Foundation. The Government has certain rights in this invention.

This is a continuation of application Ser. No. 880,851 filed July 1, 1986.

The present invention is supplementary and complementary to Smectic C liquid crystal compounds disclosed and described in U.S. Pat. No. 4,556,727 and U.S. patent application Ser. No. 782,348, the disclosures of which are incorporated in toto herein.

Ferroelectric (chiral) smectic liquid crystals (FLCs) have been shown to possess properties ideal for incorporation into electro-optic light valves such as those used in large area matrix displays utilizing the Clark-Lagerwaal surface stabilized ferroelectric liquid crystal geometry. Properties of merit for ferroelectric liquid crystals in such an application include: (1) ferroelectric polarization density; (2) orientational viscosity; (3) dielectric anistrophy; (4) chemical and photochemical stability; and (5) FLC temperature range.

While some useful liquid crystal materials have been previously reported, optimum response times have not been achieved. This is partly due to the relatively low dipole densities of many of the known materials.

It is the object of the present invention to describe a class of chirally asymmetric liquid crystal which impart the property of high dipole density upon very low polarization materials when mixed with such materials. This property demonstrates the utility of this class of chirally asymmetric liquid crystal as components of FLC mixtures.

A further object of the present invention is to disclose a class of compounds by which enantiomerically enriched units may be incorporated into the molecular framework of chirally asymmetric liquid crystals.

These and other objects and advantages of the present invention will become more apparent, and more readily appreciated, from the following detailed description of the following preferred exemplary embodiments of the present invention.

The chirally asymmetric liquid crystal compounds of the present invention are formed by incorporation of an enantiomerically enriched cyanohydrin ether unit into the tail of a bis-alkoxyphenylbenzoate liquid crystal molecular structure. More specifically, attachment of an enantiomerically enriched 1-cyanoalkoxy unit to the para position of a phenyl group of a phenyl benzoate core unit will confer the desired property of a high dipole density to the chirally asymmetric liquid crystal compounds.

The intermediate compound by which the enantiomerically enriched cyanohydrin ether units are incorporated into the phenyl benzoate liquid crystal molecular framework are also part of the present invention. More specifically, these compounds are of the general Formula I:

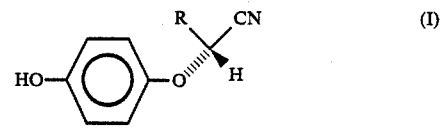

wherein R may be any alkyl of one to twelve carbon atoms. For example, R may be methyl, ethyl, propyl, butyl, pentyl, hexyl, heptyl, octyl, nonyl, decyl, undecyl, or dodecyl radicals. Furthermore, in those instances when the alkyl radical may possess structural isomerism, such as in those alkyls having three or more carbon atoms, as for example, propyl radicals, such isomers are also included within the R definition of alkyl. Although R may contain one to twelve carbon atoms, it is preferred that R contain from three to five carbon atoms.

Although the intermediate compounds according to the present invention may be selected to contain an R radical from a relatively large class of alkyl substituents, for the purposes of the ferroelectric smectic liquid crystal compounds of the present invention R is preferred to be an alkyl radical containing from one to twelve carbon atoms, preferably from one to seven carbon atoms, and more preferably three to five carbon atoms.

The incorporation of enantiomerically enriched cyanohydrin ether tail units into the liquid crystal molecular framework results in liquid crystals of the General Formula II:

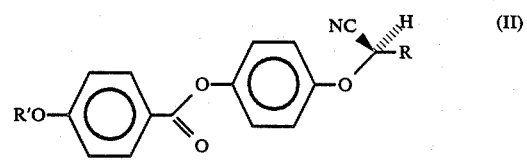

wherein R is an alkyl group as defined previously, and R' is an alkyl group of one to thirteen carbon atoms, preferably from nine to thirteen carbon atoms, and more preferably from about five to twelve carbon atoms.

The compounds according to the present invention are prepared following the exemplary synthesis flow schemes shown below.

Scheme 1

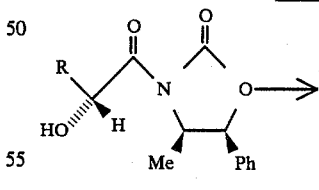

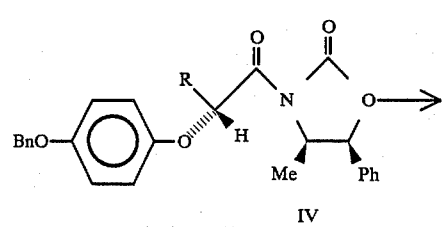

R = n-pentyl
Bn = benzyl

-continued
Scheme 1

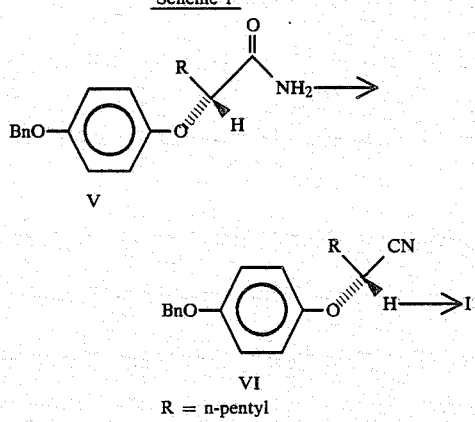

R = n-pentyl

Scheme 2

I + C₁₁H₂₃O—[phenyl]—C(Cl)=O (VII) → II
R = n-pentyl
R = n-pentyl
R' = n=undecyl In these synthesis pathways, the abbreviation Bn=benzyl.

In general terms, compounds of Formula I are prepared as follows. The highly enantiomerically enriched alpha-hydroxy-N-acyloxazolidone starting material (the compound of Formula III) is prepared according to Evans (Evans, D. A.; Morrissey, M. M.; Dorow, R. L. *J. Am. Chem. Soc.* 1985, 107, 4346–4348). Coupling of the compound of Formula III with p-benzyloxyphenol under the conditions of Mitzonobu (Mitsunobu, *Synthesis*, 1981, 1) then affords the alpha-aryloxy-N-acyloxazolidone IV. Treatment of oxazolidone IV with lithium amide, or with dimethylaluminum amide gives the alpha-aryloxy amide V, which is dehydrated to the nitrile VI by the action of trimethylsilyl polyphosphoric acid. Debenzylation by treatment with trimethylsilyl iodide then gives the phenol (the compound of Formula I R=n-pentyl). Coupling of phenol I (R=n-pentyl) with p-undecycloxybenzoyl chloride (VII) gives the target liquid crystal compound of Formula II (R=n-pentyl, R'=n-undecyl).

The following examples and procedures are presented in order to provide a more complete understanding and illustration of the present invention.

EXAMPLE I

This example illustrates the procedure for coupling of compounds III with p-benzyloxy phenol.

An oven dry 100 ml flask, fitted with reflux condenser, stir bar and septum, was charged with 1.70 g (5.57 mmol) of [3(2)R),4R,5S]-3-(2-hydroxy-1-oxyheptyl)-4-methyl-5-phenyl-(the compound of Formula III), 1.33 g (6.69 mmol) p-benzyloxyphenol and 1.75 g(6.69 mmol) of triphenylphosphine. The flask was flushed with argon and 30 ml of dry dichloromethane was introduced by syringe. To an additional 5 ml of dry dichloromethane was added 1.05 ml (1.16 g, 6.69 mmol) of diethylazodicarboxylate. This solution was added to the reaction flask dropwise over 4 hours at 25° C. The resulting light yellow reaction mixture was allowed to stir overnight.

To isolate the product, approximately 50% of the reaction solvent was removed by rotary evaporation and the resulting slurry poured into 150 ml of hexanes. The organic layer was washed with three, 50 ml portions of water, 50 ml of brine, and dried over Na₂SO₄. Filtration and solvent evaporation gave 5.18 g of a moist solid. This was subjected to flash chromatography on 300 g of silica gel was 2:8 ethylacetate/hexanes as eluent to give 1.99 g (73.3%) of pure [3(2R),4R,5S]-3-(2-benzyloxyphenyloxy)-1-oxyheptyl)-4-methyl-5-phenyl-2-oxizoli (the compound of Formula IV) as a white solid. Recrystalization from ethanol gave white needles, m.p. 74° C.

EXAMPLE II

This example illustrates the procedure for conversion of the oxazolidone compounds of Formula IV to amides of Formula V.

A 50 ml oven dry flask with a stir bar and septum was charged with 721 mg (1.48 mmol) of [3(2R), 4R,5S]-3-2-p-benzyloxyphenyloxy)-1-oxyhephl-4-methyl-5-phenyl-2-oxizolidione (the compound of Formula IV). The flask was flushed with argon, and 3.70 ml (3.70 mmol, 2.5 eq.) of a 1.0M solution of dimethyl-aluminumamide in 1:1 hexanes:dichloromethane was introduced by syringe. The resulting homogeneous solution was stirred for 7 hours at 25° C. The reaction mixture was poured into a seperatory funnel containing 20 ml of ice, 20 ml 1.0M HCl and 20 of ml ether. When methane evolution ceased the layers were separated and the aqueous layer was extracted with two additional 20 ml portions of ether. The combined organic layers were washed with brine and dried over MgSO₄. Filtration and solvent removal yielded 707 mg of a white solid. TLC analysis (1.19 acetone/dichloromethane) showed that only the chiral auxillary and product were present. Both products were isolated by flash chromatography on 50 g of silica gel with 1:19 acetone/dichloromethane as eluent, to yield 227 mg of recovered chiral auxillary (86.6%) and 431 mg of (2R)-1-benzyloxy-4-(2-oxyheptylcarboxamide)-benzene (the compound of Formula V, 89%): mp 136–142.

EXAMPLE III

This example illustrates the procedure for conversion of the amide compounds of Formula V to nitriles of Formula VI.

An oven dry 25 ml flask, fitted with a small stir bar and reflux condenser, was charged with 244 mg (0.747 mmol) of (2R)-4-(2-oxyheptylcarboxamide)benzene (the compound of Formula V). The reaction vessel was flushed with argon and 5 ml of dry benzene followed by 1.46 ml of a 1.14M solution polyphosphatetrimethylsilylester in benzene were added by syringe. The reaction mixture was heated to reflux for 8 hours until the reaction was judged complete by TLC.

To isolate the product, the cooled reaction mixture was poured into a separatory funnel with 50 ml of ether. The organic layer was washed twice with 20 ml water, 20 ml of brine and dried over MgSO₄. Filtration and solvent removal gave 217 mg (94%) of the nearly pure nitrile. Chromatography over a short column of silica gel with 15:85 ethylacetate/hexanes gave 207 mg of pure (2S)-1-benzyloxy-4-(2-oxyheptylnitrile)benzene (the compound of Formula VI, 90%). An analytical sample was recrystalized from hexanes: MP 48.5° C.

EXAMPLE IV

This example illustrates the procedure for conversion of the benzyl ether-nitriles of Formula VI to phenol-nitriles of Formula I.

A dry 10 ml flask was charged with 256 mg of 2(S)-4-benzyloxy-1-(2-oxyheptylnitrile)-benzene (the compound of Formula VI) and 2 ml of dry dichloromethane was added by syringe. To this solution was added 0.143 ml (0.200 g, 1.1 eq) of trimethylsilyliodide and the mixture was stirred for 6 hours. Methanol was added to destroy the remaining TMSI and the solvents were removed under vacuum. The resulting oil was taken up in 20 ml ether and washed with 1.0M sodium thiosulfate, brine and dried over $Na_2SO_4$. The orange oil obtained after filtration and solvent evaporation was chromatographed (10g silica gel, 1:4 ethylacetate/hexanes) to yield 0.1533 g of pure 2(S)-4-2-oxyheptylnitrile)-phenol (the compound of Formula I).

EXAMPLE V

This example illustrates the procedure for coupling of p-alkoxybenzoyl chlorides of Formula VIII with phenols of Formula I to give the liquid crystal compounds of Formula II.

A dry 10 ml flask was charged with 0.793 g (0.415 mmol) of (2S)-4-(2-oxyheptylnitrile)phenol (the compound of Formula I). 0.1500 g (0.507 mmol)p-undecyloxybenzoyl chloride (the compound of Formula VIII), a few crystals of 4-N,N-dimethylaminopyridine (DMAP), and sealed with a septum. Dry dichloromethane (2 ml) was introduced with a syringe, followed by 0.125 ml of triethylamine (1.25 mmol, 3 eq). The resulting mixture was allowed to stir for 1 hour. The reaction mixture was poured into 30 ml of hexanes. The organic layer was washed with 20 ml portions of 1.0M NaOH, water, 1.0M HCl, water, brine, and then dried with $MgSO_4$. Filtration and solvent removal gave 0.2054 g of crude product. This was initially purified by flash chromatography on 10 g of silica gel with 15.85 ethylacetate/hexanes as eluent to give 0.1589 g of product (84.9%). This was recrystalized from spectral grade methanol to produce 0.1255 g of fine white crystals of the liquid crystal compound of Formula II (R=n-pentyl, R'=n-undecyl, 79%).

The following Table I gives the phase transition temperatures for several of the novel compounds according to the general Formula II in order to illustrate the liquid crystals properties of these compounds. For several compounds in the table two sets of data are reported. When this is the case, the first set shows the phases and transition temperatures (in degrees centigrade) observed upon heating of the crystalline phase, and the second shows the phases and transition temperatures observed upon cooling of the isotropic liquid (phase transition temperatures are given in °C.; I=isotropic liquid, A=smectic A phase, N*=chiral nematic phase, and X=crystalline solid).

TABLE I

| | | Compounds II | | | | |
|---|---|---|---|---|---|---|
| | | R = n-pentyl, R' = undecyl | | | | |
| X | 60 | I | | | | |
| I | 42 | A | 36 | X | | |
| | | R = N propyl, R' = n nonyl | | | | |
| X | 60 | I | | | | |
| I | 35 | N* | 22 | X | | |
| | | R = n-propyl, R' = n-undecyl | | | | |

TABLE I-continued

| | | Compounds II | | | | |
|---|---|---|---|---|---|---|
| X | 45 | I | | | | |
| I | 40 | N* | 38.5 | A | 23 | X |
| | | R = n-pentyl, R' = n = decyl | | | | |
| X | 42 | I | | | | |
| I | 41.3 | N* | 39.0 | A | 24 | X |

As shown in Table I, none of the new liquid crystal materials possesses an enantiotropic or monotropic ferroelectric (chiral smectic C*) liquid crytal phase. However, ferroelectric liquid crystal materials used in devices are normally mixtures of two or more component compounds. Mixing of liquid crystal materials often broadens the temperature range of the liquid crystal phases. Also, mixing of materials with the type of liquid crystal phases exhibited by the compounds of Formula II with ferroelectric liquid crystals is known to often produce mixtures with enantiotropic or monotropic ferroelectric smectic C* phases. The particular advantages of the present invention in the context of ferroelectric liquid crystal mixtures is demonstrated as follows.

The compound according to Formula IX is known to possess an enantiotropic ferroelectric C* phase, but a very low dipole density (on the order of 1 nC/cm2), and very slow electro-optic switching speed (on the order of 3 msec in a 1 um thick layer in the SSFLC geometry with a 15 V/um driving voltage).

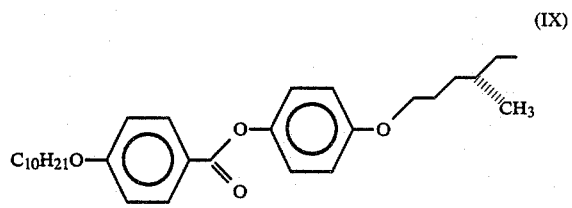

(IX)

When a mixture containing 1 part of the compound of Formula II (R=n-pentyl, R'=n-undecyl) and 1 part of the compound of Formula IX is prepared, a new composition exhibiting the phases shown in Table II is obtained:

TABLE II

Observed phases for the mixture of 1 part compound IX and 1 part compound II (R = n-pentyl, R' = n-undecyl) upon cooling of the isotropic liquid.

| I | 60 | N* | 57 | A | 42.5 | C* | 0 | X |

In addition, this mixture possesses an electrooptic switching speed in the SSFLC geometry of 130 sec at 30° C. and 116 sec at 40° C. in a one m thick layer with a 15 V/m driving voltage. Thus, the compounds of Formula II are able to induce a high polarization upon mixing in a C* phase. This property is useful in components of ferroelectric liquid crystal phases, and comprises and demonstrates the advantages of the present invention.

It is important to note that either enantiomer of any of the described chiral compounds can be readily obtained following the procedures of Evans, allowing the sign of the polarization density to be easily adjusted to optimize the ferroelectric dipole density of mixtures incorporating these compounds.

Thus, while the present asymmetrical liquid crystal compounds have been defined in their pure state, the present invention is also meant to encompass liquid crystal formulations in which the compounds of the present invention are used in admixture with one another, or formulations in which a compound of the present invention is used in admixture with other, previously known or unknown liquid crystal compounds.

Furthermore, while only a single enantiomer of each chirally asymmetrical compound has been described, the present invention is also meant to encompass both enantiomers of each compound.

From the foregoing description, one skilled in the art can easily ascertain the essential characteristics of our invention and without departing from the spirit and scope thereof, can make various changes and/or modifications to the invention for adapting it to various usages and conditions. Accordingly, such changes and modifications are properly intended to be within the full range of equivalents of the following claims.

Having thus described our invention and the manner and process of making and using it in such full, clear, concise and exact terms as to enable any person skilled in the art to which it pertains, or with which it is most closely connected, to make and use the same, and having set forth the best modes for carrying out our invention:

We claim:
1. A compound of the formula:

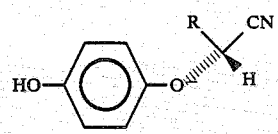

wherein R is an alkyl of one to twelve carbon atoms.

2. A compound according to claim 1 wherein R is an alkyl to one to seven carbon atoms.

3. A compound accoridng to claim 2 wherein R is an alkyl of three to five carbon atoms.

4. The compound according to claim 1 wherein R is —$CH_2CH_2CH_3$.

5. The compound according to claim 1 wherein R is —$CH_2CH_2CH_2CH_3$.

6. The compound according to claim 1 wherein R is —$CH_2(CH_2)_3CH_3$.

7. The compound according to claim 3 wherein R is —$CH_2CH_2CH_3$.

8. The compound according to claim 3 wherein R is —$CH_2CH_2CH_2CH_3$.

9. The compound according to claim 3 wherein R is —$CH_2(CH_2)_3CH_3$.

* * * * *